(12) United States Patent
Christopherson

(10) Patent No.: US 9,782,252 B2
(45) Date of Patent: Oct. 10, 2017

(54) MOVABLE OCULAR PROSTHETIC AND RELATED SYSTEMS AND METHODS THEREOF

(71) Applicant: Tim Christopherson, Tucson, AZ (US)

(72) Inventor: Tim Christopherson, Tucson, AZ (US)

( * ) Notice: Subject to any disclaimer, the term of this patent is extended or adjusted under 35 U.S.C. 154(b) by 0 days.

(21) Appl. No.: 14/941,336

(22) Filed: Nov. 13, 2015

(65) Prior Publication Data

US 2016/0331514 A1 Nov. 17, 2016

Related U.S. Application Data

(63) Continuation-in-part of application No. 14/663,414, filed on Mar. 19, 2015, now abandoned.

(51) Int. Cl.
*A61F 2/14* (2006.01)
*A61F 2/48* (2006.01)

(52) U.S. Cl.
CPC ........ *A61F 2/141* (2013.01); *A61F 2002/482* (2013.01)

(58) Field of Classification Search
CPC ...... A61F 2/14; A61F 2/141; A61F 2002/482; A61F 2230/0071; A61F 2250/0006; A63H 3/38; A63H 3/40; A63H 3/42; A63H 33/26
USPC ........................................................ 623/6.64
See application file for complete search history.

(56) References Cited

U.S. PATENT DOCUMENTS

| | | | | |
|---|---|---|---|---|
| 2,274,694 A * | 3/1942 | Henry | ........ | A63H 3/40 446/342 |
| 2,661,480 A * | 12/1953 | Rosen | ........ | A61F 2/141 623/6.64 |
| 5,376,323 A * | 12/1994 | Eaton | ........ | A61F 2/0059 264/154 |
| 6,187,041 B1 * | 2/2001 | Garonzik | ........ | A61F 2/141 623/4.1 |
| 6,419,698 B1 * | 7/2002 | Finger | ........ | A61F 2/141 623/6.41 |
| 6,879,082 B2 * | 4/2005 | Erten | ........ | H02K 41/031 310/112 |
| 8,113,907 B2 * | 2/2012 | Liu | ........ | A63H 3/40 396/427 |
| 8,179,007 B2 * | 5/2012 | Van Der Walt | ........ | F16M 11/14 310/90.5 |
| 9,161,833 B1 * | 10/2015 | Altman | ........ | A61F 2/141 |
| 2011/0066239 A1 * | 3/2011 | Smoot | ........ | A61F 2/141 623/6.64 |

(Continued)

FOREIGN PATENT DOCUMENTS

| | | | | |
|---|---|---|---|---|
| DE | 19632392 | 2/1998 | ............. | A61F 2/14 |
| JP | 2007143919 | 6/2007 | ............. | A61F 2/14 |
| WO | WO2014110190 | 7/2014 | ............. | A61F 2/16 |

OTHER PUBLICATIONS

International Search Report and Written Opinion issued in application No. PCT/US16/46174, dated Oct. 26, 2016 (10 pgs).

*Primary Examiner* — Paul Prebilic
(74) *Attorney, Agent, or Firm* — Hayes Soloway P.C.

(57) ABSTRACT

A movable ocular prosthetic apparatus and related systems and methods for moving an ocular prosthetic include a support member. An ocular prosthetic is mounted to the support member, wherein the ocular prosthetic is movable about the at least two axes of rotation. A control system controls a movement of the ocular prosthetic based on a sensed movement of a pupil of an eyeball of a human being.

17 Claims, 9 Drawing Sheets

(56) References Cited

U.S. PATENT DOCUMENTS

2014/0214162 A1    7/2014  Smoot et al. ............... 623/6.64
2015/0342723 A1*  12/2015  Abramson ............. A61F 2/141
                                                        623/6.64
2016/0354702 A1*  12/2016  Smoot .................... A61F 2/141

\* cited by examiner

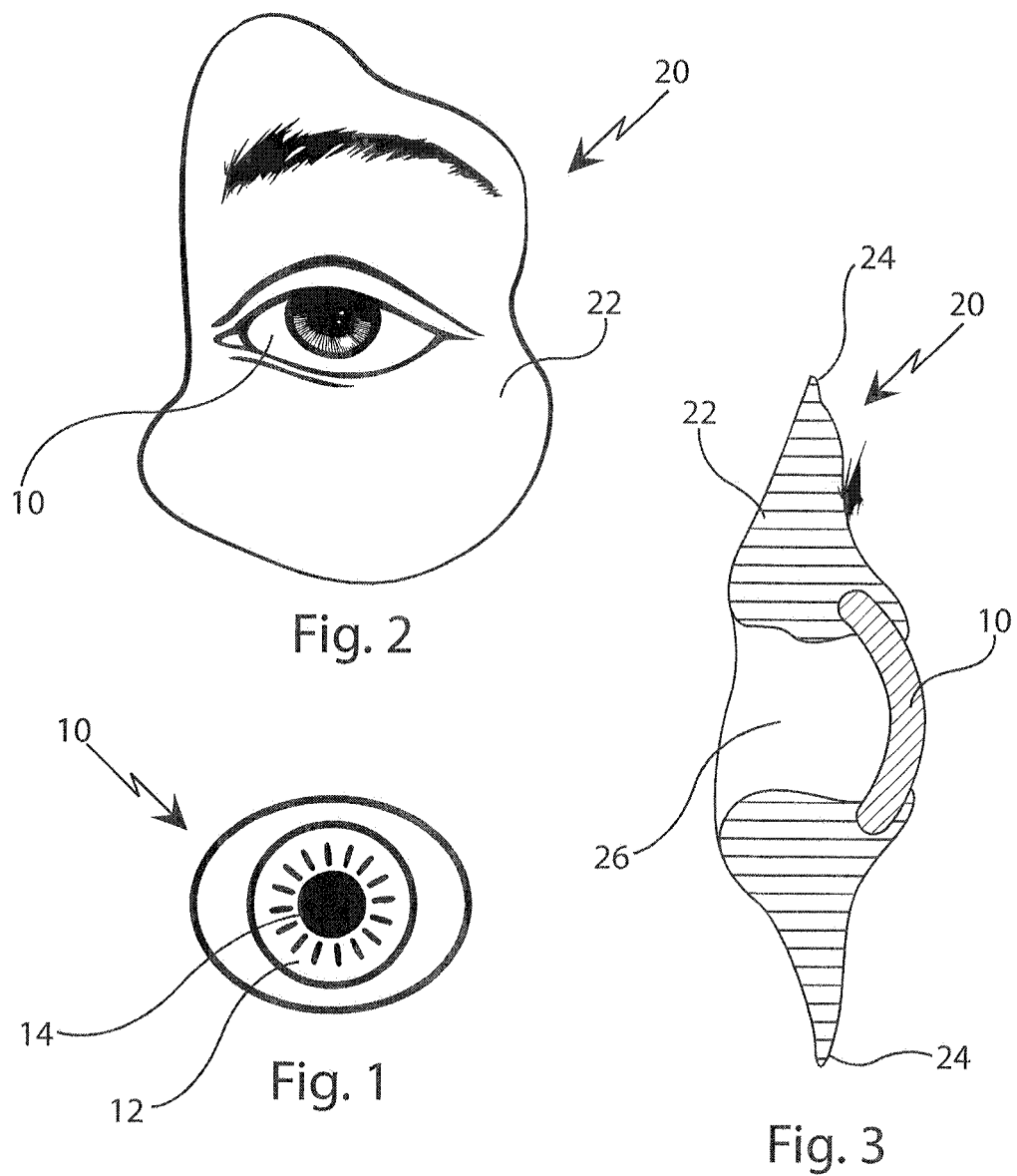

MOVABLE OCULAR PROSTHETIC AND RELATED SYSTEMS AND METHODS THEREOF

FIELD OF THE DISCLOSURE

The present disclosure is generally related to prosthetics and more particularly is related to a movable ocular prosthetic and related systems and methods thereof.

BACKGROUND OF THE DISCLOSURE

When a human being loses an eyeball due to illness or injury, the defect is often disguised through the use of a cosmetic replacement called an ocular prosthetic. FIG. 1 is an illustration of an ocular prosthetic 10 in accordance with the prior art. The ocular prosthetic 10 is commonly formed from a hardened resin material and designed to match the user's eyeball such that the ocular prosthetic 10 obtains the look of a natural eyeball. The ocular prosthetic 10 has an iris 12 having a pupil 14, commonly with a fixed diameter, where the iris 12 is colored to match the coloring of the iris of the wearer's remaining natural eyeball.

When both an eyeball and the surrounding muscles and tissue are lost due to illness or injury, the defect is cosmetically disguised with an orbital prosthetic. FIGS. 2-3 are a front view illustration and a cross-sectional side view illustration of an orbital prosthetic 20 in accordance with the prior art. The orbital prosthetic 20 commonly consists of two parts: the ocular prosthetic 10 and a facial prosthetic 22. The facial prosthetic 22 is commonly formed from a moldable material, such as silicon, which is formed with a shape that can fit within a cavity of the user's eye socket and can be interfaced with the facial skin of the user to blend the prosthesis with the user's face. The facial prosthetic 22 may be secured within the user's eye socket cavity using an adhesive, using one or more osseointegrated implants, or using another method or device which securely adheres the facial prosthetic 22 in the desired place. The edges 24 of the facial prosthetic 22 may be tapered to allow blending of the prosthetic with the user's face with makeup or similar coverings. The ocular prosthetic 10 may be mounted in the facial prosthetic 22 and the center of the facial prosthetic 22 may include a prosthetic cavity 26 positioned substantially behind the ocular prosthetic 10.

It is highly desirable that ocular prosthetics 10 and orbital prosthetics 20 provide a natural-looking appearance so that people who view a user with an ocular prosthetic 10 and/or orbital prosthetic 20 do not notice the use of a prosthetic and so the user of the ocular prosthetic 10 and/or orbital prosthetic 20 does not feel conspicuous. While ocular prosthetics 10 and orbital prosthetics 20 provide users with a significant improvement in their facial defect in comparison to not using a prosthetic, they also fail to appear natural in many ways. For example, most conventional ocular prosthetics 10 do not mimic or mirror a user's natural eyeball, which is readily noticeable to observers. This movement may include resizing of the pupil or movement of the eyeball within the eye socket. As a result, while the ocular prosthetics 10 and/or orbital prosthetics 20 may be satisfactory in limited situations where the user does not have significant interaction with another person, in situations where more extensive interactions occur, e.g., handshake greetings, conversations, and the like, an observer can often easily notice the use of the prosthetic.

Thus, a heretofore unaddressed need exists in the industry to address the aforementioned deficiencies and inadequacies.

SUMMARY OF THE DISCLOSURE

Embodiments of the present disclosure provide a system and method for moving an ocular prosthetic. Briefly described, in architecture, one embodiment of the system, among others, can be implemented as follows. The system for moving an ocular prosthetic has a support member having at least two axes of rotation. An ocular prosthetic is mounted to the support member, wherein the ocular prosthetic is movable about the at least two axes of rotation. A control system controls a movement of the ocular prosthetic.

The present disclosure can also be viewed as providing a movable ocular prosthetic apparatus. Briefly described, in architecture, one embodiment of the apparatus, among others, can be implemented as follows. An ocular prosthetic support has at least two axes of rotation. An ocular prosthetic is mounted to the support, wherein the ocular prosthetic is movable about the at least two axes of rotation.

The present disclosure can also be viewed as providing methods of moving an ocular prosthetic. In this regard, one embodiment of such a method, among others, can be broadly summarized by the following steps: mounting an ocular prosthetic to a support having at least two axes of rotation; positioning the support at least partially within an eye socket of a human being; sensing a movement of a pupil of an eyeball of the human being; and moving the support to thereby move the ocular prosthetic based on the sensed movement of the pupil of the eyeball of the human being.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 is an illustration of an ocular prosthetic in accordance with the prior art.

FIGS. 2-3 are a front view illustration and a cross-sectional side view illustration of an orbital prosthetic in accordance with the prior art.

DETAILED DESCRIPTION

Figure 4:
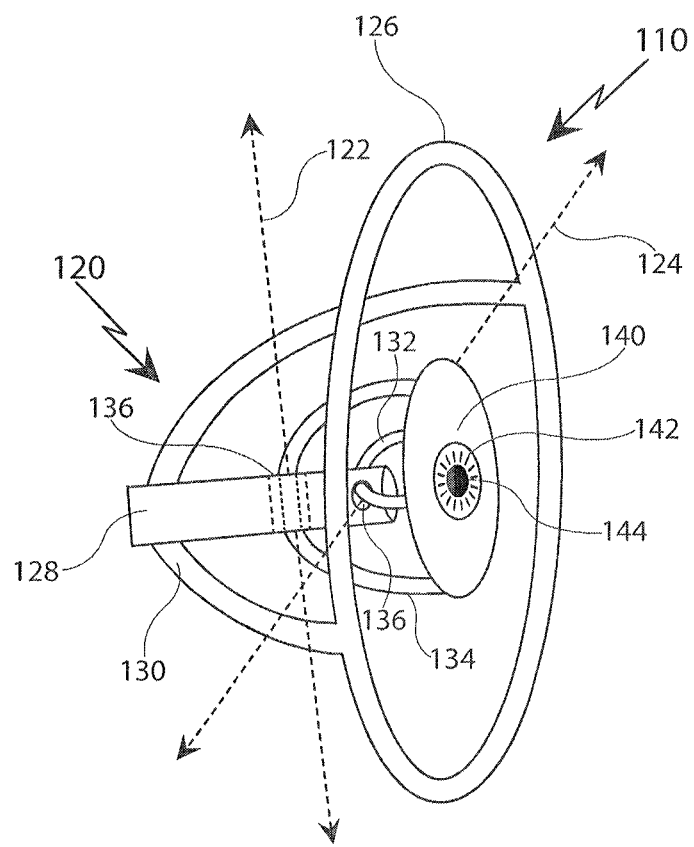
FIG. 4 is an isometric view illustration of a movable ocular prosthetic apparatus, in accordance with a first exemplary embodiment of the present disclosure.
Figure 5:
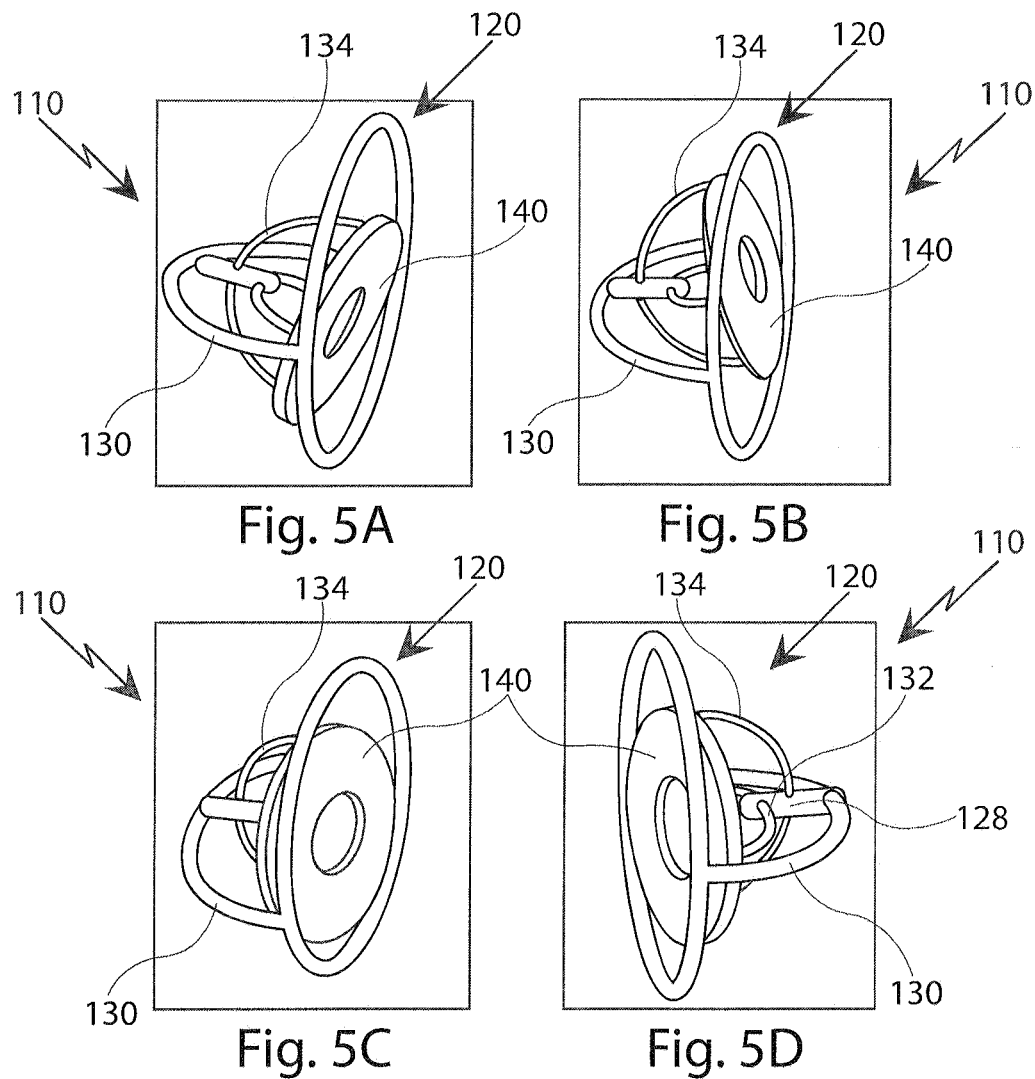
FIGS. 5A-5D are isometric view illustrations of the movable ocular prosthetic apparatus of FIG. 4, in accordance with the first exemplary embodiment of the present disclosure.

FIG. 4 is an isometric view illustration of a movable ocular prosthetic apparatus 110, in accordance with a first exemplary embodiment of the present disclosure. The movable ocular prosthetic apparatus 110, which may be referred to herein simply as 'apparatus 110', includes a gimbal 120 having at least two axes of rotation 122, 124. An ocular prosthetic 140 is mounted to the gimbal 120, wherein the ocular prosthetic 140 is movable about the at least two axes of rotation 122, 124. The gimbal 120 may be characterized as a support that allows rotational motion of an object. As shown in FIG. 4, the gimbal 120 may include a number of frame members, including an ocular frame member 126 which is positioned surrounding the ocular prosthetic 140, which is provided with aesthetic reproductions of an iris 142 and a pupil 144.

The ocular frame member 126 may be connected to a central rail 128 with arm 130, thereby retaining the ocular frame member 126 in a substantially stationary position relative to the central rail 128. In this manner, the ocular frame member 126 and arm 130 may effectively act as a housing or guard for the ocular prosthetic 140 and may also act as a structure for mounting the apparatus 110 within a user's eye socket. It is noted that FIG. 4 is not necessarily to scale and that the relative size of the ocular prosthetic 140 to the gimbal 120 may be changeable depending on the specific design of the apparatus 110.

The ocular prosthetic 140 may be movable relative to the central rail 128 using movable arms, namely a pitch arm 132 and a yaw arm 134. Each of the movable arms may be connected to the ocular prosthetic 140 and be movably interfaced with the central rail 128. For example, as shown in FIG. 4, each of the pitch arm 132 and yaw arm 134 are semi-circular members which are connected to the ocular prosthetic 140 at terminating ends thereof and movably interfaced with the central rail 128 towards a center thereof. The movable interface with the central rail 128 may include a positioning of each of the pitch arm 132 and the yaw arm 134 within a hole 136 formed in the central rail 128. Each of the pitch arm 132 and the yaw arm 134 may be both rotatable and laterally slidable within their respective holes 136 to facilitate movement of the ocular prosthetic 140. It is noted that while one exemplary type of gimbal 120 is illustrated in FIG. 4, other gimbal devices may also be used within the apparatus 110, all of which are considered within the scope of the present disclosure.

FIGS. 5A-5D are isometric view illustrations of the movable ocular prosthetic apparatus 110 of FIG. 4, in accordance with the first exemplary embodiment of the present disclosure. Relative to FIGS. 4-5D, the combination of the pitch arm 132 and the yaw arm 134 may be used to recreate the natural movement of a human eyeball by providing realistic combinations of vertical and horizontal movement. The pitch arm 132 may facilitate movement of the ocular prosthetic 140 along a vertical direction, e.g., tiling movement between up and down positions rotatable about one axis of rotation 124, while the yaw arm 134 may facilitate movement of the ocular prosthetic 140 along a horizontal direction, e.g., panning movement between left and right positions rotatable about another axis of rotation 122. The combination of tilting movement and panning movement allows for the mimicking of natural eyeball movement in all combinations of tilt and pan.

As shown in FIG. 5A, the ocular prosthetic 140 is illustrated in a horizontally-neutral and tilted down position which is achieved by rotating the yaw arm 134 upwards through the hole 136 within the central rail 128 of the gimbal 120. In contrast, in FIG. 5B, the ocular prosthetic 140 is illustrated in a horizontally-neutral and tilted up position which is achieved by rotating the yaw arm 134 downwards through the hole 136 within the central rail 128. In FIG. 5C, the ocular prosthetic 140 is illustrated in a vertically-neutral and panned left position which is achieved by rotating the pitch arm 132 laterally in a right-hand direction through the hole 136 within the central rail 128 of the gimbal 120. Again, in contrast, in FIG. 5D, the ocular prosthetic 140 is illustrated in a vertically-neutral and panned right position which is achieved by rotating the pitch arm 132 laterally in a left-hand direction through the hole 136 within the central rail 128. In each of the panning or tilting movement, either the pitch arm 132 or the yaw arm 134 will be rotated within a hole 136 with the other being moved translationally through the other hole 136. When both the pitch arm 132 and the yaw arm 134 are moved simultaneously, the ocular prosthetic 140 is both tilted and panned, i.e., diagonal movement. The ability of the gimbal 120 to move the ocular prosthetic 140 in any combination of panning and tilting, vertical and horizontal directions, makes it possible to recreate all movements of a human eyeball, including blinking.

Figure 6:
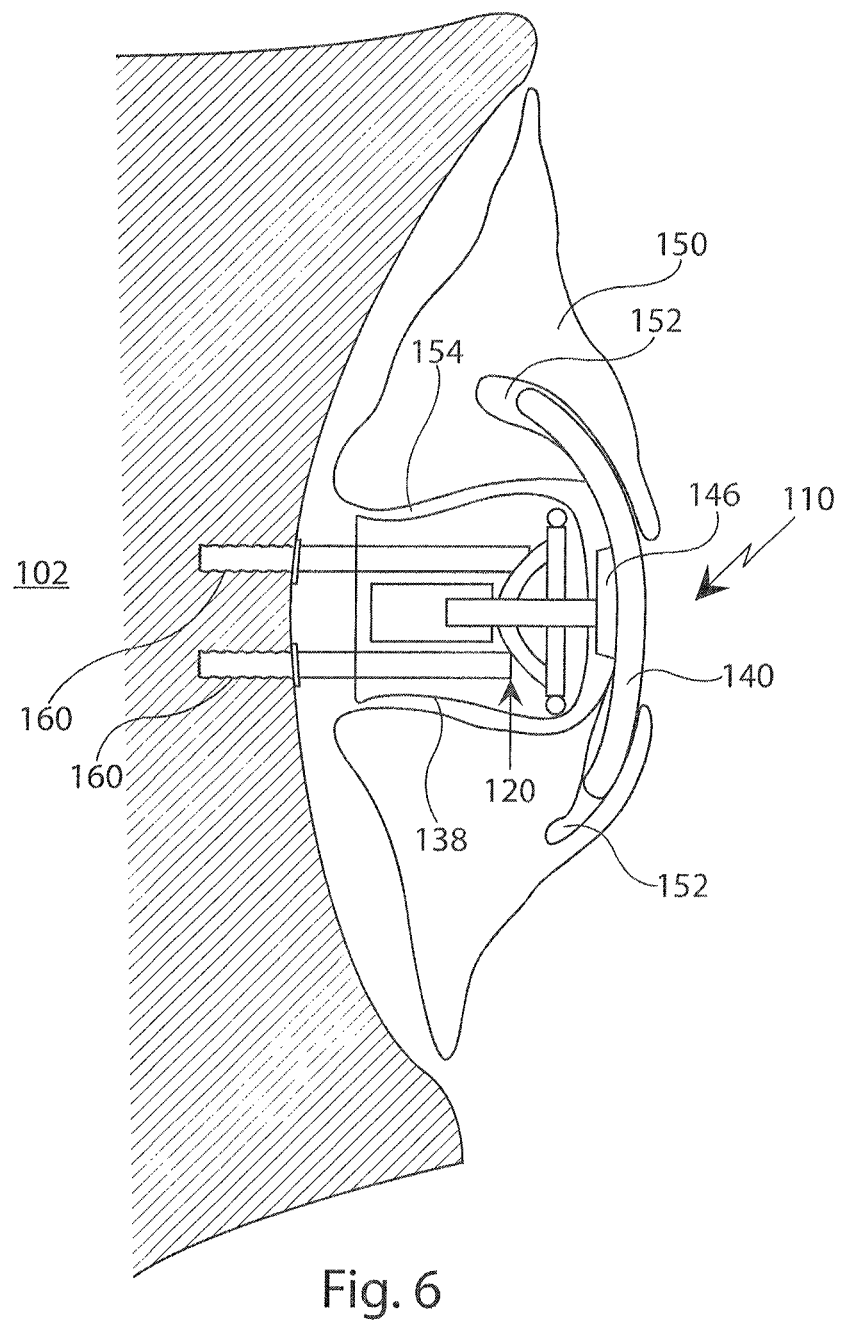
FIG. 6 is a cross-sectional side view illustration of the movable ocular prosthetic apparatus of FIG. 4 mounted with a facial prosthetic, in accordance with the first exemplary embodiment of the present disclosure.

FIG. 6 is a cross-sectional side view illustration of the movable ocular prosthetic apparatus 110 of FIG. 4 mounted with a facial prosthetic 150, in accordance with the first exemplary embodiment of the present disclosure. A facial prosthetic 150 may be used with re apparatus 110 when a user of the apparatus 110 requires an orbital prosthetic, such as when the muscles and tissue of the eye socket which normally support an eyeball are absent. In this situation, the facial prosthetic 150 can be a cosmetic application of recreating the human eye socket which the apparatus 110 is used with. The gimbal 120 may be sized to fit within the central prosthetic cavity 154 of the facial prosthetic 150 such that it occupies no more space than the facial prosthetic 150 itself. For example, the gimbal 120 may be sized small enough to be embedded within the facial prosthetic 150. The gimbal 120 may be positioned within an enclosure 138 which provides a barrier between the moving and non-moving members of the gimbal 120 and the facial prosthetic 150. A mounting plate 146 may also be used with the apparatus 110 in a position between the gimbal 120 and the ocular prosthetic 140. The ocular prosthetic 140 may be removably mounted to the mounting plate 146, such that it can be connected and disconnected to the gimbal 120 with convenience.

As shown in FIG. 6, the apparatus 110 may be mounted to the wearer with a plurality of osseointegrated implants 160 which are connected to the eye socket 102 of the wearer. The osseointegrated implants 160 may be affixed to the bone of the eye socket 102 and extend through the facial skin of the user. The gimbal 120, or another component of the apparatus 110, may be removably connected to the ends of the osseointegrated implants 160, thereby allowing for mounting and dismounting of the apparatus 110 to the user's eye socket 102. In one of many alternatives, the apparatus 110 may be positioned and retained on the user with an adhesive material interfaced between the facial prosthetic 150 and the exterior skin of the user's eye socket 102, and the apparatus 110 may be retained within the facial prosthetic 150. It is noted that the apparatus 110 may be designed to be mounted and dismounted to a wearer for any length of time. For example, the apparatus 110 may be mounted and dismounted to the wearer on a daily basis or a longer-term basis, such as for weeks at a time. Furthermore, it is noted that other devices and/or methods of mounting the apparatus 110 to the user may also be used, all of which are within the scope of the present disclosure.

When the apparatus 110 is used with the facial prosthetic 150, as shown in FIG. 6, the facial prosthetic 150 may be designed with an appropriate structure to operate with a movable ocular prosthetic 140. For example, the facial prosthetic 150 may include an ocular cavity 152 sized larger than a footprint of the ocular prosthetic 140 to allow the ocular prosthetic 140 to be moved relative to the facial prosthetic 150. In one of many alternatives to the use of ocular cavities 152 within the facial prosthetic 150, excess prosthetic material may be used around the opening of the facial prosthetic 150 to permit movement of the ocular prosthetic 140.

Figure 7:
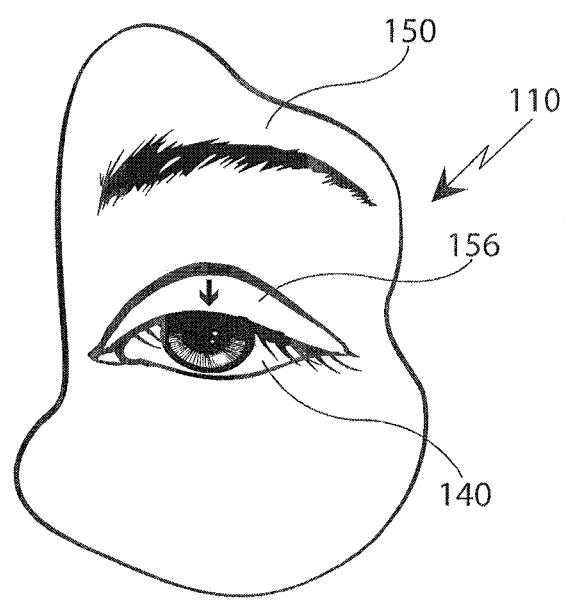
FIG. 7 is a front view illustration of the movable ocular prosthetic apparatus of FIG. 4 mounted with a facial prosthetic with a movable eyelid, in accordance with the first exemplary embodiment of the present disclosure.

FIG. 7 is a front view illustration of the movable ocular prosthetic apparatus 110 of FIG. 4 mounted with a facial prosthetic 150 with a movable prosthetic eyelid 156, in accordance with the first exemplary embodiment of the present disclosure. When the apparatus 110 is used with a facial prosthetic 150, it may be desirable for the facial prosthetic 150 to include a prosthetic eyelid 156 which is movable between raised and lowered positions over an exterior surface of the ocular prosthetic 140 to simulate blinking. The prosthetic eyelid 156 may be formed from the same or similar material to that of the facial prosthetic 150 and may be connected to the facial prosthetic 150 at an upper edge of the prosthetic eyelid 156. Movement of the prosthetic eyelid 156 may be controlled by the apparatus 110, such as with an actuator interfaced with the gimbal that is capable of raising and lowering the prosthetic eyelid 156. As discussed relative to FIGS. 8-9, the movement of the prosthetic eyelid 156 may be controlled using a control system in a similar fashion to how movement of the ocular prosthetic 140 is controlled.

Figure 8:
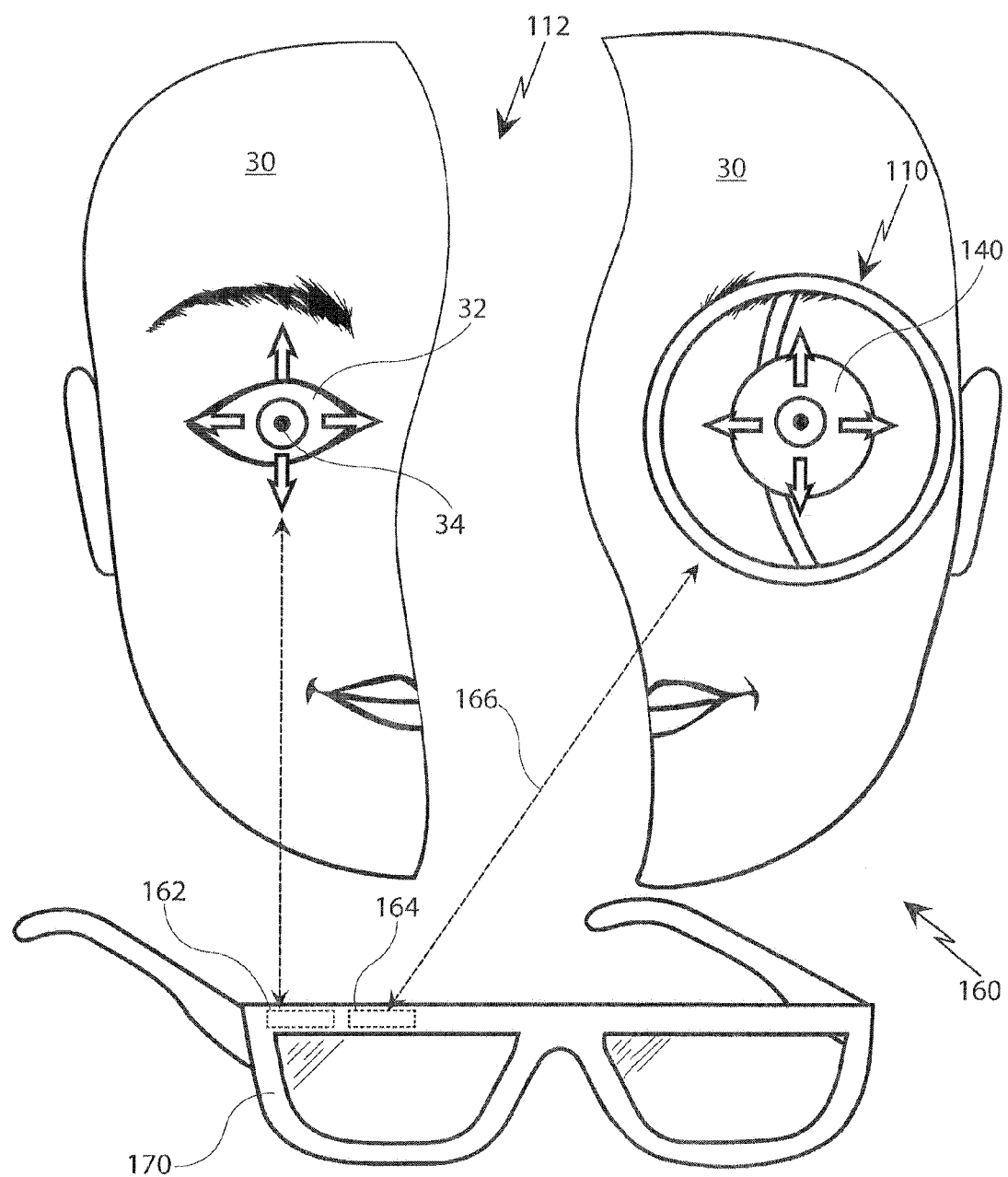
FIG. 8 is a diagrammatical illustration of a system for moving an ocular prosthetic, in accordance with the first exemplary embodiment of the present disclosure.
Figure 9:
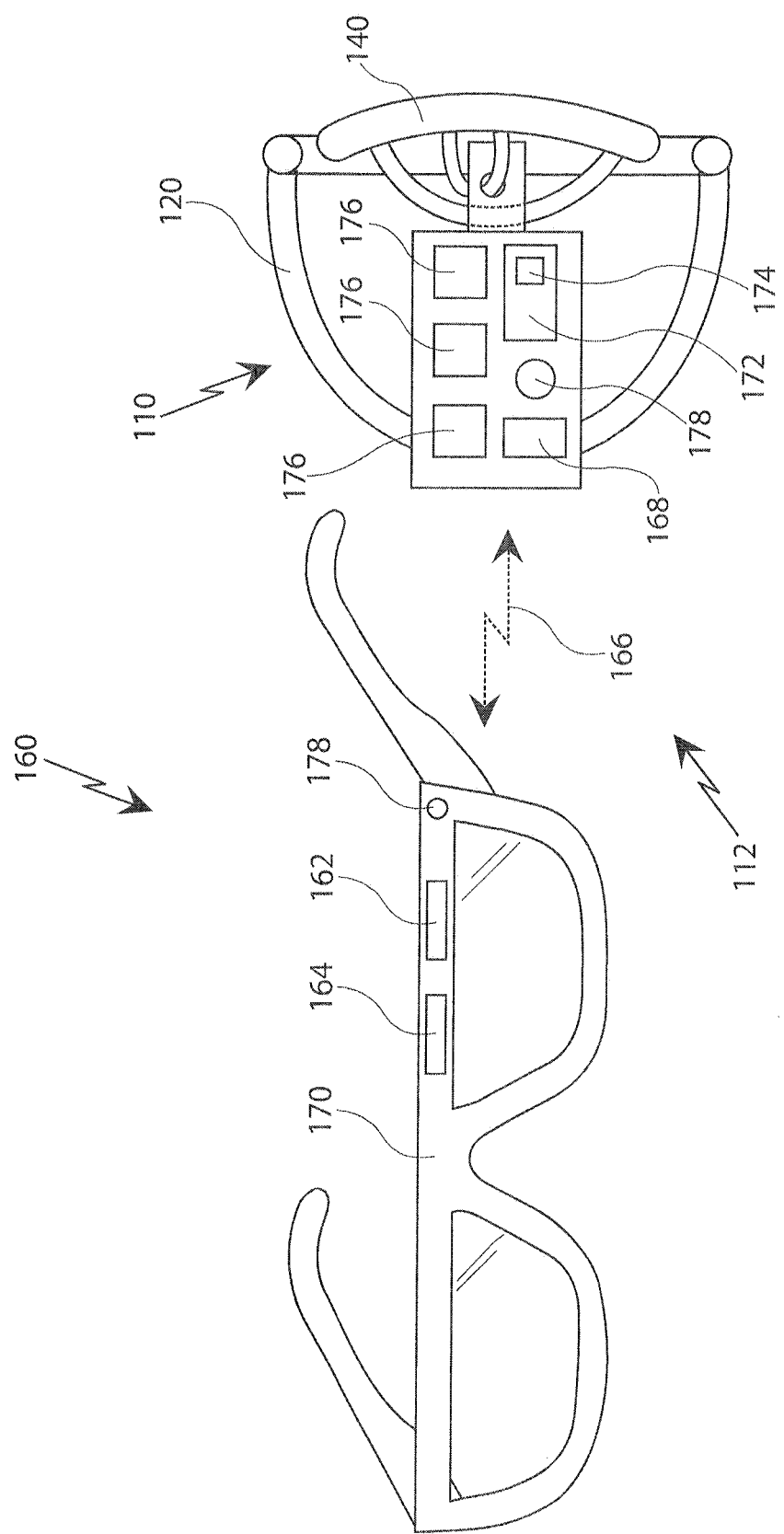
FIG. 9 is a schematic illustration of the system for moving an ocular prosthetic of FIG. 8, in accordance with the first exemplary embodiment of the present disclosure.

FIG. 8 is a diagrammatical illustration of a system for moving an ocular prosthetic 112, in accordance with the first exemplary embodiment of the present disclosure. Specifically, FIG. 8 depicts two views of a human user 30 having a natural eyeball 32 in one eye socket and the apparatus 110 positioned in another eye socket. FIG. 9 is a schematic illustration of the system for moving an ocular prosthetic 112 of FIG. 8, in accordance with the first exemplary embodiment of the present disclosure. The system for moving an ocular prosthetic 112, which may be referred to herein simply as 'system 112' may work in conjunction with the components of the apparatus 110 disclosed relative to FIGS. 4-7 to control the movement of the ocular prosthetic 140 and other aspects of the apparatus 110. Relative to FIGS. 8-9, the system 112 uses the gimbal 120 having at least two axes of rotation (FIG. 4) and the ocular prosthetic 140 mounted to the gimbal 120, where the ocular prosthetic 140 is movable about the at least two axes of rotation. In addition, the system 112 includes a control system 160 for controlling a movement of the ocular prosthetic 140. The control system 160 may control the movement of the ocular prosthetic 140 based on movement of a natural eyeball 32 of the user 30. Specifically, the control system 160 may sense the movement of the pupil 34 of the natural eyeball 32 and instruct the gimbal 120 to move the ocular prosthetic 140 in a mirroring pattern. Accordingly, the system 112 can help blend the wearer's use of a prosthetic with their natural eye movements.

The control system 160 may include a sensor 162 mounted on an eyeglass frame 170 such that it is positioned to sense a movement of the pupil 34 of the natural eyeball 32. The sensor 162 may include an infrared (IR) sensor or another type of sensing device. The sensor 162 may be capable of identifying the movement and/or positioning of the pupil 34 as well as other aspects of the movement of the natural eyeball 32, such as a speed at which movement occurs, a dilation size of the pupil 34, and a movement of a natural eyelid of the user 30. The sensor 162 may be positioned on any appropriate part of the eyeglass frame 170 or lenses thereof.

Once the movement and/or direction of the pupil 34 is sensed, a wireless transmitter 164, such as a radio frequency (RF) transmitter may be used to communicate at least one control signal 166 of the eyeglass frame 170 to a wireless receiver 168, such as an RF receiver, connected to the gimbal 120. The wireless receiver 168 may be in communication with an integrated circuit 172 having a memory 174. The integrated circuit 172 may be connected to one or more motors 176, such as torque motors, which are included with the gimbal 120 and capable of moving arms of the gimbal 120. The memory 174 may include a tracking algorithm stored thereon which is executable by a processor of the integrated circuit 172. One or more directional instructions are sent from the integrated circuit 172 to the motors 176 to instruct the motors 176 to move the pitch arm 132 and/or the yaw arm 134, which in turn, moves the ocular prosthetic 140. Accordingly, the movement of the ocular prosthetic 140 is based on the control signal 166 which is based on the sensed movement of the pupil 34 of the natural eyeball 32.

It is further noted that the system 112 may include many other features to effectuate successful functioning of the system 112 or provide proper functioning of the apparatus 110 based on movement of the natural eyeball 32. For example, the sensor 162 may be capable of sensing an eyelid movement of the natural eyeball 32 and instructing the gimbal 120 to move a prosthetic eyelid of the apparatus 110 when a facial prosthetic is used (not shown in FIGS. 8-9). In another example, the gimbal 120 and/or the eyeglass frames 170 may include a power supply 178 such as a battery. Other features may include an input/output device, non-transitory memory with various software or programming, communication protocols, status indicators, and any other components which can be used with a movable prosthetic device. Furthermore, the apparatus 110 and system 112 may be designed for convenient usage by the wearer, in that, they may be light enough such that the weight of the apparatus 110 does not cause it to inadvertently fall off the user's face.

Figure 10:
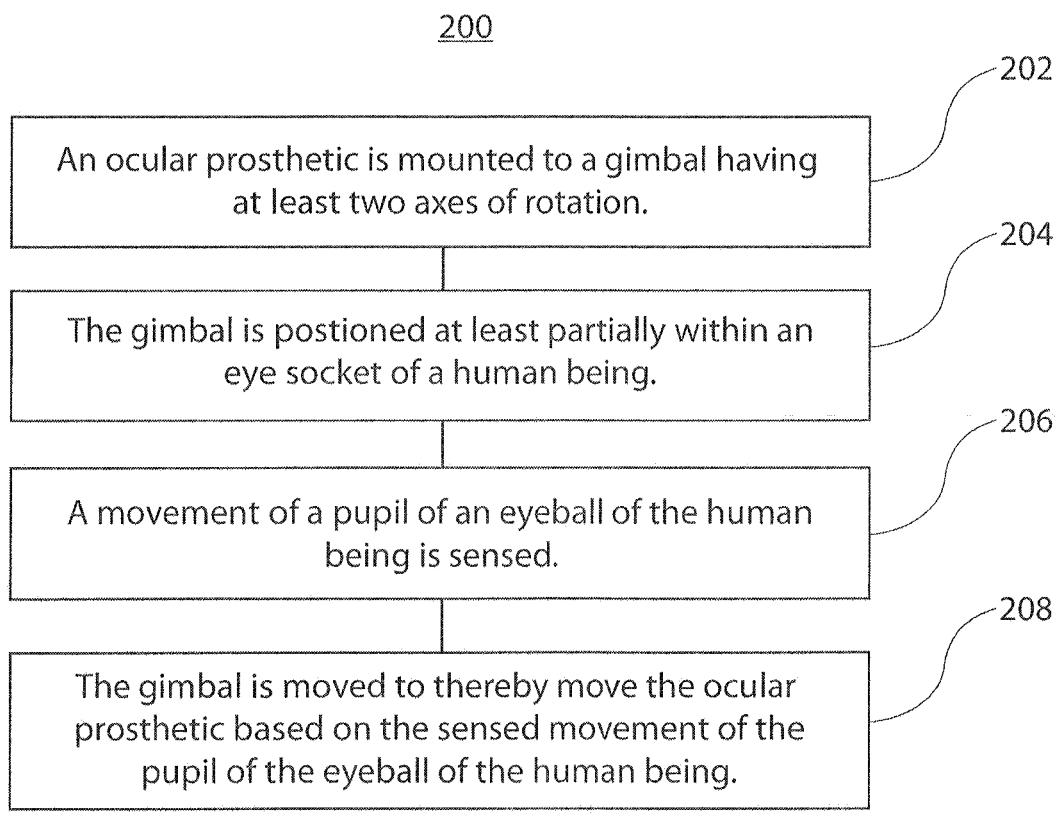
FIG. 10 is a flowchart illustrating a method of moving an ocular prosthetic, in accordance with the first exemplary embodiment of the present disclosure.

FIG. 10 is a flowchart 200 illustrating a method of moving an ocular prosthetic, in accordance with the first exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 202, an ocular prosthetic is mounted to a gimbal having at least two axes of rotation. The gimbal is positioned at least partially within an eye socket of a human being (block 204). A movement of a pupil of an eyeball of the human being is sensed (block 206). The gimbal is moved to thereby move the ocular prosthetic based on the sensed movement of the pupil of the eyeball of the human being (block 208). The method may include any number of additional steps, processes, functions, or structures, including any disclosed relative to any figure of this disclosure. For example, sensing the movement of the pupil of the eyeball of the human being may include sensing the movement of the pupil of the eyeball of the human being with an infrared sensor positioned on an eyeglass frame worn by the human being. Moving the gimbal to move the ocular prosthetic based on the sensed movement of the pupil of the eyeball of the human being may include wirelessly transmitting at least one control signal to a receiver positioned within the gimbal. The at least one control signal may be processed within a tracking algorithm, wherein the tracking algorithm is stored within a memory of an integrated circuit positioned within the gimbal. Then, a directional instruction may be sent from the integrated circuit to at least one motor operatively connected to the gimbal. Accordingly, the sensed movement of the pupil of the eyeball of the human may be used to allow the ocular prosthetic to mirror a movement of the pupil of the eyeball of the human being. The method may also include the use of a facial prosthetic. In this example, the facial prosthetic may include a prosthetic eyelid, wherein the prosthetic eyelid is movable over an exterior surface of the ocular prosthetic to simulate blinking.

Figure 11:
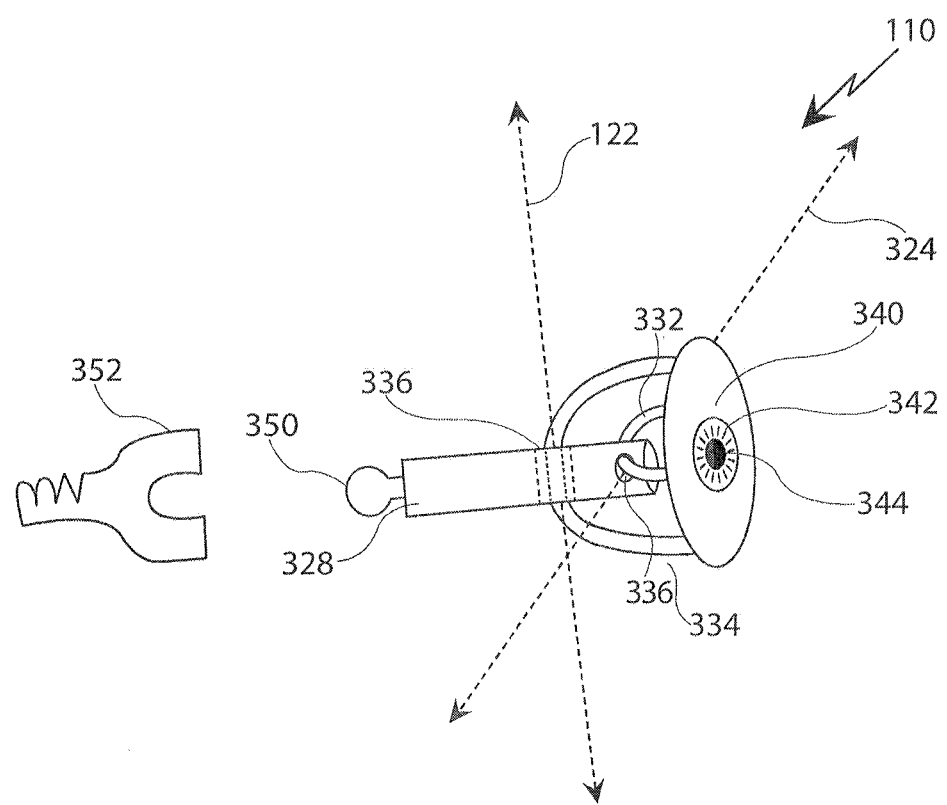
FIG. 11 is a view, similar to FIG. 4, of an ocular prosthetic in accordance with second exemplary embodiment of the present disclosure.

It should be emphasized that the above-described embodiments of the present disclosure, particularly, any "preferred" embodiments, are merely possible examples of implementations, merely set forth for a clear understanding of the principles of the disclosure. Various variations and modifications may be made to the above-described embodiment(s) of the disclosure without departing substantially from the spirit and principles of the disclosure. For example, FIG. 11 is a view, similar to FIG. 6, showing, in cross-sectional, a movable ocular prosthetic apparatus mounted directly in an eye socket, in accordance with another embodiment of my invention. The ocular prosthetic apparatus 300 shown in FIG. 11 is similar to the ocular prosthetic portion of the ocular prosthetic/orbital prosthetic shown in FIGS. 4-6. However, the FIG. 11 embodiment is intended solely as an ocular prosthetic, i.e., for mounting in an otherwise undamaged eye-socket.

The movable ocular prosthetic apparatus 310, in accordance with this second embodiment referred to herein simply as 'apparatus 310', includes an ocular prosthetic 340, which is provided with aesthetic reproductions of an iris 342 and a pupil 344.

The ocular prosthetic 340 is supported by and movable relative to one end of central rail or support member 328 using movable arms, namely a pitch arm 332 and a yaw arm 334. Each of the movable arms 332, 334 may be connected and be movably interfaced with the central rail 328. For example, as shown in FIG. 11, each of the pitch arm 332 and yaw arm 334 are semi-circular members which are connected to the ocular prosthetic 340 at terminating ends thereof and movably interfaced with the central rail 328 towards a center thereof. The movable interface with the central rail 328 may include a positioning of each of the pitch arm 332 and the yaw arm 334 within a hole 336 formed in the central rail 328. Each of the pitch arm 332 and the yaw arm 334 may be both rotatable and laterally slidable within their respective holes 336 to facilitate movement of the ocular prosthetic 340. The other end of central rail 328 is fitted with a fixture such as a ball 350 for selectively engaging with a socket 352 which is implanted in the eye socket of the individual.

Movement of ocular prosthetic 340 is achieved by rotating yaw arm 334 and pitch arm 332, similar movement to ocular prosthetic 140 described above.

All such modifications and variations are intended to be included herein within the scope of this disclosure and the present disclosure and protected by the following claims.

What is claimed is:

1. A system for moving an ocular prosthetic comprising:
   a gimbal having at least two degrees of rotation, wherein the gimbal comprises an ocular frame supporting a pitch arm and a yaw arm;
   an ocular prosthetic supported by the pitch arm and the yaw arm, wherein the ocular prosthetic is movable about said at least two axes of rotation;
   a support member adapted to support said gimbal within a user's eye socket; and
   a control system controlling a movement of the ocular prosthetic, said control system comprising:
      a sensor positioned to sense a movement of a human pupil;
      a motor connected to the support member; and
      at least one control signal communicator between the sensor and the motor.

2. The system of claim 1, wherein the sensor positioned to sense the movement of the human pupil is mounted on an eyeglass frame.

3. The system of claim 2, wherein the at least one control signal is communicated from an RF transmitter positioned on the eyeglass frame and an RF receiver connected to the support member.

4. The system of claim 1, wherein the sensor further comprises an infrared sensor.

5. The system of claim 1, further comprising an integrated circuit having a memory connected to the motor, wherein a tracking algorithm stored on the memory sends directional instructions to the motor based on the at least one control signal.

6. The system of claim 1, wherein support member comprises a facial prosthetic.

7. The system of claim 1, wherein the at least two axes of rotation comprise at least a pitch rotation and a yaw rotation.

8. The system of claim 1, further comprising a mounting plate positioned between the ocular prosthetic and the gimbal.

9. The system of claim 1, wherein the support member is adapted to be removably mountable within a human eye socket through an osseointegrated implant.

10. A movable ocular prosthetic apparatus comprising:
    a gimbal having at least two degrees of rotation, wherein the gimbal comprises an ocular frame supporting a pitch arm and a yaw arm, wherein the ocular frame includes a central rail, and the pitch arm and the yaw arm are supported at one end thereof by the central rail;

a support member adapted to support said gimbal within a user's eye socket; and an ocular prosthetic supported by the pitch arm and the yaw arm, wherein the ocular prosthetic is movable about at least two axes of rotation.

11. The movable ocular prosthetic apparatus of claim 10, wherein the at least two axes comprise at least a pitch rotation and a yaw rotation.

12. The movable ocular prosthetic apparatus of claim 10, wherein the support member comprises a facial prosthetic.

13. The system of claim 6, wherein the facial prosthetic has tapered edges adapted to allow blending of the facial prosthetic with a wearer's face.

14. The movable ocular prosthetic apparatus of claim 12, wherein the facial prosthetic has tapered edges adapted to allow blending of the facial prosthetic with a wearer's face.

15. The system of claim 1, wherein the gimbal comprises an ocular frame member connected to a central rail with an arm retaining the ocular frame member in a stationary position relative to the central rail, and said pitch arm and said yaw arm are connected at one end thereof to the ocular prosthetic, and movably interfaced at their other ends with the central rail.

16. The movable ocular prosthetic apparatus of claim 10, wherein the ocular frame member is connected to the central rail with an arm retaining the ocular frame member in a stationary position relative to the central rail, and said pitch arm and said yaw arm are connected at one end thereof to the ocular prosthetic, and are movably interfaced at their other ends with the central rail.

17. The system of claim 1, wherein the ocular frame includes a central rail, and the pitch arm and the yaw arm are supported at one end thereof by the central rail.

\* \* \* \* \*